United States Patent [19]

Frankiewicz

[11] 4,320,241

[45] Mar. 16, 1982

[54] PROCESS FOR CONVERTING OXYGENATED HYDROCARBONS INTO HYDROCARBONS

[75] Inventor: Theodore C. Frankiewicz, Westminster, Calif.

[73] Assignee: Occidental Research Corporation, Irvine, Calif.

[21] Appl. No.: 182,291

[22] Filed: Aug. 28, 1980

[51] Int. Cl.$^3$ .......................... C07C 1/20; C07C 1/00
[52] U.S. Cl. ..................................... 585/469; 201/25; 585/640; 585/733

[58] Field of Search ...................... 585/469, 640, 733; 201/25

[56] References Cited

U.S. PATENT DOCUMENTS 4,060,568 11/1977 Rodewald ........................ 585/469
4,197,418 4/1980 Lee et al. ........................ 585/469

Primary Examiner—Curtis R. Davis

[57] ABSTRACT

Oxygenated hydrocarbons are contacted with a crystalline aluminosilicate zeolite for conversion into hydrocarbons.

14 Claims, No Drawings

PROCESS FOR CONVERTING OXYGENATED HYDROCARBONS INTO HYDROCARBONS

FIELD OF THE INVENTION

The instant invention relates to a process for converting highly oxygenated hydrocarbons into oxygen free hydrocarbons by reacting said oxygenated hydrocarbons in the presence of a crystalline aluminosilicate zeolite catalyst having a silica to alumina ratio of at least about twelve. In one embodiment of this invention the highly oxygenated hydrocarbons are derived from the pyrolysis of cellulosic materials, preferably the cellulosic materials present in a municipal solid waste source. In another embodiment of the invention, the crystalline aluminosilicate zeolite catalyst is provided in admixture with a low surface area diluent, e.g., silica to minimize the conversion of the highly oxygenated hydrocarbon to coke. In the most preferred embodiment, municipal solid waste is treated to segregate a fraction which is substantially cellulosic in nature and this fraction is pyrolyzed in an inert atmosphere at a temperature of at least about 300° C. for a time sufficient to yield an oxygenated hydrocarbon vapor. Said oxygenated hydrocarbon vapor is passed to a deoxygenation zone wherein it is contacted with a crystalline aluminosilicate zeolite catalyst having a silica to alumina ratio of at least 12 and supported on a low surface area silica at conditions sufficient to convert said oxygenated hydrocarbon substantially to a hydrocarbon fraction boiling in the range of gasoline, that is from about 30° C. to 220° C.

BACKGROUND OF THE PRIOR ART

The conversion of oxygenated hydrocarbons to oxygen free hydrocarbons by reacting the oxygenated molecules in the presence of an acid catalyst is well known. More recently, it has been shown that certain classes of such oxygenated molecules may be converted rather easily to hydrocarbon products over acidic solid surfaces such as those present in crystalline aluminosilicate zeolites with high silica to alumina ratios. Those molecules which convert easily include monofunctional aliphatic alcohols, ethers, aldehydes, and analogs thereof. Zeolites effective in this conversion include mordenite, offretite, and certain synthetic zeolites such as those described in U.S. Pat. Nos. 3,894,107 or 3,899,544. Generally, these conversions are effective only for molecules with 8 carbons or less. Larger molecules may be converted, according to the literature (Science 206, 10/5/79) if a hydrogen atmosphere is present and if the carbon to oxygen ratio in the molecule is reasonably high, e.g., more than 8–10.

Other classes of oxygenated molecules exist which are more difficult to convert to oxygen-free hydrocarbons. These include short chain acetates, carboxylic acids, carbohydrates, cellulose, and other highly oxygenated polymeric species. U.S. Pat. No. 3,998,898 to Chang, et al, teaches that these molecules may be converted to hydrocarbons if (1) they have 8 carbons or less, and (2) they are reacted in the presence of a substantial quantity of "easily convertible" molecules such as short chain alcohols. In this patent, a relation R is defined wherein $R > 1$ for any oxygenated molecule which is easily convertible to hydrocarbons and $R < 1$ for any oxygenated molecule which is difficult to convert to hydrocarbons. This patent teaches that the overall mixture of hydrocarbons to be converted must have a cumulative R value $> 1$ for successful conversion to hydrocarbons even though that mixture may contain some oxygenated molecules with $R < 1$.

As disclosed in U.S. Pat. No. 3,998,898, R is calculated from the formula $R = (m - 2p)/n$ wherein m is the number of hydrogen atoms in the molecule, p is the number of oxygen atoms in the molecule, and n is the number of carbon atoms in the molecule.

The preferred catalyst for the above discussed conversion is a synthetic, shape selective zeolite whose properties are discussed therein and which is admixed with high surface area alumina binder. As will be shown below, the presence of the alumina binder contributes significantly to coke formation during the processing of oxygenated molecules which are difficult to convert to hydrocarbons, i.e., $R < 1$. In addition, it will be shown that in accordance with the instant invention oxygenated hydrocarbons of any carbon to oxygen ratio, R value, or carbon chain length can be converted to oxygen-free hydrocarbons through a unique combination of a crystalline, aluminosilicate zeolite and a proper diluent for such zeolite.

SUMMARY OF THE INVENTION

The instant invention relates to improvements in a process for converting oxygenated hydrocarbon molecules of any functionality, carbon to oxygen ratio, R value, or carbon chain length into an oxygen-free hydrocarbon product.

The oxygenated hydrocarbon molecules useful as a feed for the process of the instant invention may include substituent hetero atoms such as nitrogen, sulfur, halide etc., but preferably such molecules will contain only carbon, hydrogen, and oxygen atoms. The oxygenated hydrocarbons especially preferred for use in this process will contain from one to 20 carbon atoms, preferably from 5 to 18 carbon atoms. Such oxygenated hydrocarbons may be monofunctional or polyfunctional in respect to the oxygen functionality. In general, the oxygenated hydrocarbons will be alcohols, aldehydes, acetates, ethers, and organic acids. The instant process is especially suitable for converting polyfunctional aliphatic oxygenated compounds having a relatively high ratio of oxygen to carbon atoms to the corresponding hydrocarbons, i.e., highly oxygenated hydrocarbons. For the purposes of this invention, highly oxygenated hydrocarbons shall mean hydrocarbons having an R value of $< 1$ as defined by the formula given in U.S. Pat. No. 3,998,898.

For example the instant process is suitable for deoxygenating compounds such as tetrahydrofurfuryl alcohol and α-methylglucoside and most especially preferred for deoxygenating α-methylglucoside (which has an R number of 2/7) and similar compounds.

The instant process comprises contacting said oxygenated hydrocarbons with a specific crystalline aluminosilicate zeolite catalyst in the vapor state. The reaction is preferably carried out at conditions whereby said oxygenated hydrocarbon is substantially deoxygenated to yield a hydrocarbon product, however, less than complete deoxygenation may, in certain instances, be desirable.

In the process of the instant invention, a selected oxygenated hydrocarbon feed is contacted with the crystalline aluminosilicate zeolite catalyst described below at a temperature of at least about 200° C. and preferably from 275° C. to 425° C. The above process may be carried out at a weight hourly space velocity of from about 0.1 to 50 WHSV preferably from 1 to 10 WHSV. Furthermore, the conversion may be carried out at a pressure from about 1 to about 100 atmospheres. The above temperature pressure-space velocity parameters will be varied to provide the desired hydrocarbon product mixture. For example, when the product form is gasoline, the above parameters will be adjusted to give hydrocarbon product containing $C_6$ to $C_{10}$ monocyclic aromatic hydrocarbons as a major product, as these particular materials are known in the art for their high octane rating.

The deoxygenation process of the instant invention may be carried out in the presence of hydrogen, CO, steam or a suitable inert gas, i.e., one that will not react with the desired reaction products, e.g., $N_2$, Argon, etc. Oxidizing gases should be avoided to increase the yield of the deoxygenated product. It has been found that the presence of steam has a tendency to decrease coking during the above reaction, but inert gases, even though they do not decrease coking, are suitable for carring out the above conversion process.

The crystalline aluminosilicate zeolite catalyst will have a $SiO_2/Al_2O_3 > 12$ and a pore size sufficiently small to prevent the formation of condensed ring molecules in the pores of the zeolite. Such zeolites have been characterized as having a "constraint index" of about 1–12. Constraint index is defined in U.S. Pat. No. 3,998,898, and such definition is incorporated herein by reference. A preferred embodiment of the instant invention comprises providing said crystalline aluminosilicate zeolite catalyst in a 'noncoking' form, e.g., as an admixture with a low surface area diluent, such as for example supported on a low surface area silica support which of itself possesses little or no Bronsted acidity and is substantially incapable of catalyzing any reaction of oxygenated molecules.

In one aspect of this invention the hydrocarbon which results from the practice of the instant process is gasoline, as this term is commonly used in the petroleum industry. That is, the resulting product is a motor fuel for internal combustion engines; the product being a mixture of aliphatic and aromatic hydrocarbons having a full boiling range of from about 30° C. to about 220° C. A suitable gasoline may contain additives such as alcohols and ethers which are initially present in the oxygenated hydrocarbon feed. Thus complete conversion to a hydrocarbon is not necessary to make a suitable gasoline by the process of the instant invention; however, even when it is desired to make gasoline by the instant process, substantially all of the oxygenated hydrocarbon is desirably converted into a hydrocarbon.

In another aspect of the instant invention the feed stream is a specific highly oxygenated hydrocarbon mixture derived from the pyrolysis of cellulose, especially a cellulosic fraction isolated from municipal solid waste. As described further below, this cellulosic fraction may be obtained by the processes known in the art for the separation of municipal solid waste into its valuable components. For example, processes are known in the art for removing magnetics; electroconducting non-magnetics; glass; and other inorganics from the municipal solid waste to yield a fraction containing substantially cellulosic materials. This fraction may be pyrolyzed at a temperature of at least 300° C. in an inert gas by processes known in the art such as pyrolysis processes described in U.S. Pat. Nos. 4,153,514 and 4,147,593, which are hereby incorporated by reference. This particularly preferred feed stream, which is derived from the pyrolysis of the cellulosic fraction of municipal solid waste may contain a variety of oxygenated hydrocarbons as well as CO, $H_2$, $CO_2$, $H_2O$, miscellaneous de-oxygenated products, ash and char. The oxygenated hydrocarbons may be substantially separated from the remainder of the pyrolysis product and converted by the process of the instant invention into a substantially oxygen-free hydrocarbon fraction. It should be noted that while the separation of ash and char from the pyrolysis product prior to its reaction over the zeolite catalyst is desirable, the separation of gaseous by-products of pyrolysis such as CO, $CO_2$, $H_2$, $H_2O$, $CH_4$, etc. is not necessary. These gases may be introduced into the reactor along with the highly oxygenated hydrocarbons resulting from such pyrolysis. The mixture of such gaseous by-products and such highly oxygenated hydrocarbons, after separation of ash and char is hereinafter designated as "pyrovapor".

The oxygen contained in such oxygenated hydrocarbons is removed as CO, $CO_2$ and $H_2O$ during the deoxygenation process to yield a product having substantially improved energy value. It is noted that while the deoxygenation of the pyrolysis product of the cellulosic fraction of municipal solid waste may be most efficiently obtained by use of the noncoking crystalline aluminosilicate zeolite catalysts described herein, the use of the prior art zeolite catalyst especially those described in U.S. Pat. No. 3,998,898, in such deoxygenation process is also novel and useful.

It has been found that crystalline aluminosilicate zeolite catalysts having silica to alumina ratios of more than 12 have a tendency to decompose the highly oxygenated hydrocarbons, such as derived from the pyrolysis of municipal solid waste, to yield coke. Coke, which is highly condensed aromatics and carbon, will eventually destroy the activity of the zeolite catalyst by deposition on the surface thereof. Also substantial amounts of the feed which would otherwise result in product may be used up in the formation of such coke. Thus as noted above, the above aluminosilicate zeolite catalysts may be treated to decrease this propensity for coke formation, i.e. the crystalline aluminosilicate is converted to a "noncoking" form. For example, in a most preferred embodiment, the above crystalline aluminosilicate zeolite catalyst is admixed with a low-surface area diluent such as silica.

THE CRYSTALLINE ALUMINOSILICATE ZEOLITE CATALYST

The catalysts suitable for use in the instant invention are generally described as crystalline aluminosilicate zeolite minerals having $SiO_2/Al_2O_3$ at least 12 and a pore size with a kinetic diameter of 6 Å. The desired pore size is present in the so-called intermediate port zeolites whose pore openings are defined by 10 membered rings of oxygen atoms which are covalently bonded to a tetrahedral $SiO_2$-$Al_2O_3$ framework. Three examples of such zeolites are ZSM-5, TMA offretite and silicalite. These zeolites have pores with kinetic diameters of 6 A. The first zeolite is described in detail in U.S. Pat. No. 3,702,886, which is herein incorporated by reference, while data on the second is available from D. W. Breck (*Zeolite Molecular Sieves*, J. Wiley & Sons, New York, 1974). The third zeolite silicalite is described in U.S. Pat. No. 4,061,724 which is herein incorporated by reference.

Large port zeolites, such as mordenite, have pore openings defined by 12 oxygen atoms in a manner analogous to that described above. Mordenite has a pore kinetic diameter of 6.2 Å and would seem to be suitable for use in effecting the desired conversion chemistry. However, the pore geometry of this zeolite is such that rapid coking occurs as condensed ring hydrocarbons form in the pores. In contrast, pore geometries of the intermediate port zeolites will not allow the formation of condensed ring hydrocarbons. Thus, as will be shown by example, their ability to convert "pyrovapor" to product hydrocarbons is retained for a relatively long period of time before regeneration is required. In general, the crystalline aluminosilicate zeolite catalysts useful in this invention will have a pore size within the range of from about 5.3 Å to 6.0 Å.

It is well known in the art that hetero-atomic hydrocarbons are potent precursors for coke formation. Since this invention utilizes, as a feed stream, molecules which consist almost exclusively of coke precursor type molecules, intermediate port or "shape selective zeolites" are not themselves capable of the efficient conversion of oxygenated hydrocarbons, such as the highly oxygenated hydrocarbons present in pyrovapor, to hydrocarbons. The above cited U.S. Pat. No. 3,998,898 attempted to solve the coking problem in a limited way by the addition of certain easily deoxygenated hydrocarbons to a highly oxygenated hydrocarbon feed stream. It has now been found, however, that a much more general and useful approach is feasible which extends the ability of shape selective catalysts to de-oxygenate highly oxygenated hydrocarbons such as found in pyrovapor, but does not rely on the addition of easily de-oxygenated hydrocarbons to the feed stream.

Surprisingly, it has been found that the character of the zeolite supporting or diluting solids has a marked effect on the rate of coke formation during the conversion of pyrovapor to product hydrocarbons. Also, the addition of steam to the reacting mixture also has the effect of decreasing coke yields and increasing product hydrocarbon yields correspondingly.

The above catalyst can be mixed with a low-surface area silica or other inert solid including a low surface area alumina to yield a composite having low coking tendencies and suitable activity for converting oxygenated hydrocarbons to hydrocarbons. Such admixture can be mechanical or the zeolite may be supported on the low-surface area silica. Methods for supporting the zeolite on a support solid are known in the art and do not constitute part of this invention.

Preferably, the low surface area support of diluent solid will have a surface area less than 25 m²/g as measured by the BET method. The ratio of the zeolite to low surface area solid may vary from 0.01 to 0.50 by weight. Preferably this ratio will be from 0.03 to 0.15.

THE FEED STREAM

The instant process is carried out in the gaseous phase; therefore, oxygenated hydrocarbons, which are gaseous at reaction temperatures may be utilized as suitable feed stocks for the instant process. For example, alcohols, aldehydes, organic acids, ethers, ketones having from one to twenty carbon atoms and including both mono-functional and poly-functional oxygenates may be suitably used as feed stock. Materials of this sort include essentially all common carbon, hydrogen and oxygen containing molecules and most all vaporous products from the pyrolysis of municipal solid waste organics, biomass, or peat. The most preferred feed stock for treatment by the process of the instant invention is derived from the pyrolysis of the cellulosic fraction of municipal solid waste, biomass, or peat. A feed stock of this nature, which may be prepared by the process disclosed in U.S. Pat. Nos. 4,153,514 and 4,147,593, and may contain the following components: poly-functional oxygenates, furan derivatives, acids and esters, ketones and aldehydes, olefinic carboxyls and low molecular weight carbohydrate polymers, etc. In general, a feed stock of this sort will have an oxygen to carbon atomic ratio of from 2.5 to 3.0 and will contain impurities such as HCl, $H_2S$, $NH_3$, CO, $CO_2$, $H_2$, inorganic dust, char, etc.

The most preferred embodiment of the instant invention, that is, the process for converting the pyrolysis product of the cellulosic fraction derived from municipal solid waste into a hydrocarbon may be carried out as follows:

(a) Solid waste, including cellulosic materials, is separated by means known in the art into an inorganic fraction and an organic fraction, which may contain entrained particulate inorganic constituents.

(b) Such organic fraction is comminuted for example to a particle size of less than 8 mesh and dried preferably to a moisture content of less than about 20%.

(c) The dried organic fraction is then pyrolyzed in the presence of an inert carrier gas, i.e., a carrier gas which is nondeleteriously reactive with the pyrolysis products and a heat source, for example a carbon containing residue of pyrolysis of the organic fraction of solid waste or a particulate inorganic solid heat source which may be formed from the decarbonization of said carbon-containing residue of pyrolysis. The pyrolysis step is taught in U.S. Pat. Nos. 4,153,514 and 4,147,593, which are herein incorporated by reference. Pyrolysis is carried out under transport turbulent flow conditions in a pyrolysis zone maintained at a temperature of from about 300° C. to less than the sintering temperature of the inorganic solid heat source, e.g., from about 300° C. to about 800° C. In U.S. Pat. No. 4,147,593, it is taught that the heat source is the solid inorganic material which results from the decarbonization of the carbon-containing solid residue of pyrolysis in the presence of oxygen. U.S. Pat. 4,153,514 teaches that the solid heat source may be particulate char, the carbon-containing solid residue which is formed in situ during said pyrolysis process. The instant invention may be carried out in either mode. The process is carried out for a time sufficient to obtain a product of said pyrolysis process ("pyrovapor") which includes condensible pyrolytic oils and gases, including the highly oxygenated hydrocarbons noted above, and said carbon-containing solid residue.

The pyrolysis process may be carried out at a weight ratio of solid heat source to dried organic fraction of from about 2 to 1 to about 20 to 1. The solids residence time in the pyrolysis zone may be from 0.1 to about 2 seconds.

(d) The inorganic heat source which may be the carbon-containing solid residue of pyrolysis or a decarbonized inorganic solid derived therefrom is separated along with any solid carbon-containing residue, from the "pyrovapor". In the mode of operation described in U.S. Pat. No. 4,153,514 the carbon-containing solid residue of pyrolysis will be decarbonized, for example by high temperature oxidation, in the presence of a source of oxygen, e.g., air, to form additional inorganic solid heat source at a temperature below the fusion temperature of the inorganic solid heat source and recycled to the process. The particle size of the inorganic solid heat source may range from about 20 to about 2000 microns.

(e) The "pyrovapor" is deoxygenated after separation from the carbon-containing solid residue of pyrolysis and/or the inorganic heat source by contacting with a crystalline aluminosilicate zeolite catalyst having a silica to alumina ratio of at least 12, and preferably greater than 15, at conditions sufficient to convert the oxygenated hydrocarbons contained therein into hydrocarbons. The deoxygenation process is described in detail above, however, the deoxygenation of "pyrovapor" may be carried out at a temperature of at least 275° C., and preferably from 350° to 400° C. The "pyrovapor" may be further admixed with an inert gas prior to contacting with the crystalline aluminosilicate zoelite catalysts, e.g., $N_2$, $CO_2$, $H_2O$. Steam has been found to decrease the coking propensity of the catalyst without affecting conversion to hydrocarbons at a level of up to about 90% by weight of the pyrovapor. The hydrocarbons resulting from the deoxygenation of "pyrovapor" are conveniently recovered by cooling to condense the product liquids. Equipment and apparatus suitable for carrying out the above process is described in the art, e.g., see the above noted patents. The following are specific examples of the instant invention, however, there is no intention to be bound thereto.

EXAMPLE 1

In this experiment, a compound which is representative of the highly oxygenated hydrocarbons found during the initial stages of the pyrolysis of the cellulosics found in municipal solid waste was utilized to demonstrate the instant deoxygenation process and catalyst.

A 33% solution, by weight, of α-methylglucoside ($C_7H_{12}O_5$) in $H_2O$ was fed into a reactor comprising a pyrolysis zone and a deoxygenation zone, wherein a deoxygenation catalyst is maintained. The catalyst comprised a composite of 10%, by weight, of a crystalline aluminosilicate zeolite catalyst, having a silica to alumina ratio of 38, a pore size of 5.4 Å to 5.7 Å, and 90%, by weight of a silica having a surface area of $\leq 1.0$ $m^2/g$. The catalyst (and the other catalysts described herein below) were prepared by physically admixing the zeolite thoroughly with the diluent solid and pressing the resultant powder into pellets of the desired size and shape. The pyrolysis zone was maintained at a temperature of 550° C. and the solution was continuously fed thereinto at a rate of 1.35 grams of solution per gram of catalyst per hour. The pyrolysis vapor generated in the pyrolysis zone was cooled to 375° C. prior to contacting the deoxygenation catalyst. The excess steam generated during the pyrolysis was utilized as the carrier gas. After 1 hour, the various products from the above process were analyzed.

Based upon the fraction of carbon found in each product category, the distribution is as follows:

Carbon converted to:
pyrolysis char—15%
catalyst coke—11%
gaseous products—20%
aqueous soluble organics—24%
organic liquids—30%

The organic liquids were further analyzed and found to be 52% aromatic and substantially free of organic oxygen content.

This example clearly shows the efficacy of the instant process for converting highly oxygenated molecules to oxygen-free hydrocarbons of commercial value without the need for admixing "easily convertible" hydrocarbons.

EXAMPLE 2

It has been found empirically that the vapor from the pyrolysis of the cellulosic fraction of municipal solid waste (pyrovapor) has the approximate stoichiometry of $C_6H_{10}O_2$. Thus, a model compound, tetrahydrofurfuryl alcohol (Thfa), with the stoichiometry $C_5H_{10}O_2$ was used to simulate pyrovapor in this example. Thfa was passed over intermediate port zeolites admixed with the diluents described below at 375° C. at a weight hourly space velocity (WHSV) of 1 hr.$^{-1}$, until the feed/zeolite ratio was achieved. The following results were obtained.

TABLE 1

| Run # | Catalyst | Feed | % Reacted | % Deoxygenation | % Reacted Carbon on Catalyst |
|---|---|---|---|---|---|
| 38 | 10% Zeolite/ 90% Low Surface Area Silica[1] | Thfa | 96% | 68% | 2.2% |
| 39 | 10% Zeolite/ 90% Fumed $SiO_2$[2] | Thfa | 100% | 67% | 4.7% |
| 41 | 10 Zeolite/ 90% Low Surface Area Silica | Thfa/$H_2O$[4] | 100% | 75% | 2.0% |
| B | 10% Zeolite/ 90% Low Surface[3] $Al_2O_3$ | Thfa | 100% | 55% | 3.1% |

[1] Surface Area of $\leq 10 \frac{m^2}{gm}$
[2] Surface Area of $\sim 150 \frac{m^2}{gm}$
[3] Surface Area of about $3 \frac{m^2}{gm}$
[4] A mixture of 50/50 Thfa/$H_2O$, thus showing that up to 50% by weight of the feed to the deoxygenation process may be $H_2O$ and this will beneficially affect catalyst coking.

In addition to the above, the acid character of various diluents were characterized by using a series of indicators which change color at various acid strengths. In this manner, the approximate acid strength of a particular solid surface can be determined and Hammett acid function value, $H_o$, can be assigned. The results are summarized as follows:

TABLE 2

| | | | % Reacted Carbon on the Catalyst | |
|---|---|---|---|---|
| Run # | Diluent | $H_o$ | $\frac{\text{Wt. Feed}}{\text{Wt. Catalyst}} \sim 0.1$ | $\frac{\text{Wt. Feed}}{\text{Wt. Catalyst}} \sim 10$ |
| 28 | Low surface Area Silica | <6.8 | 6.4 | |
| 38 | Low surface Area Silica | <6.8 | | 2.2 |
| 39 | Fumed Silica | 4.0–3.3 | | 4.7 |
| B | Low Surface | 4.0–3.3 | | 3.1 |

TABLE 2-continued

| Run # | Diluent | % Reacted Carbon on the Catalyst $H_o$ | $\frac{\text{Wt. Feed}}{\text{Wt. Catalyst}} \sim 0.1$ | $\frac{\text{Wt. Feed}}{\text{Wt. Catalyst}} \sim 10$ |
|---|---|---|---|---|
| 35 | Area Alumina Kaolin[4] | 3.3-1.5 | 16 | |
| 6 | High Surface Al$_2$O$_3$[5] | ≤1.5 | 45 | |

[4]Surface Area 150 $\frac{m^2}{gm}$

[5]Surface Area 150 $\frac{m^2}{gm}$

An examination of the results listed here indicates that both low surface area and low surface acidity are important diluent characteristics for the conversion of highly oxygenated hydrocarbons to hydrocarbons. Solids with Hammett function values less than 3 will result in unacceptably high coking rates (and short catalyst life) even if the diluent is of low surface area. However, a high Hammett function value for the solid support while being necessary, is not sufficient. Fumed silica is weakly acidic but its high surface area will still cause a considerable increase in coke formation. Generally, the surface area of the diluent should be less than about 25 m$^2$/gm.

EXAMPLE 3

In this example Thfa was reacted over an intermediate port zeolite (Series 26) and a large port zeolite (Series 29) under the conditions described in Example 2, except that the ratio of feed to catalyst was ~1. The results are shown in Table 3 and dramatically show the importance of zeolite pore size on the efficacy of the catalyst. In both cases low surface area SiO$_2$ was used as the diluting solid. Clearly the intermediate port zeolite which will not allow condensed ring carbon formation is more effective over a longer period of time than is the large port zeolite.

TABLE 3

| Run # | Catalyst | % Reacted carbon on the catalyst | Final/Initial Reactivity |
|---|---|---|---|
| 26 | 10% Zeolite[a] 90% SiO$_2$ | 5.7 | .83 |
| 29 | 10% Zeolite[b] 90% SiO$_2$ | 31.2 | <.05 |

[a]This catalyst had 0.08% mg exchanged for the hydrogen cations of the zeolite. This low level of exchange is not believed to effect the comparison of this experiment. The pore size was 5.4 × 5.7Å.

[b]Dealuminized mordenite having a pore size of approximately 6.7 × 7.0Å.

What is claimed is:

1. A process for converting oxygenated hydrocarbons into hydrocarbons which comprises the step of contacting said oxygenated hydrocarbons with a catalyst comprising an admixture of a crystalline aluminosilicate zeolite and a low surface area, low acidity diluent, said diluent being characterized as having a surface area of less than about 25 m$^2$/gm and Hammet acid function value of at least about 3, at conditions sufficient to convert at least a portion of said oxygenated hydrocarbons into hydrocarbons.

2. The process of claim 1 wherein the crystalline aluminosilicate zeolite has a silica to alumina molar ratio of at least about 12.

3. The process of claim 2 wherein said crystalline aluminosilicate is selected from the group consisting of ZSM-5, TMA-offretite, and silicalite.

4. The process of claim 2 wherein said crystalline aluminosilicate has a pore size of from about 5.3 to 6.0 Å.

5. The process of claim 2 wherein the weight ratio of crystalline aluminosilicate to diluent varies from about 0.01 to about 0.50.

6. The process of claim 2 wherein said oxygenated hydrocarbons have from 5 to 18 carbon atoms.

7. The process of claim 6 wherein said converting occurs at a temperature of from about 275° C. to about 425° C., a weight hourly space velocity of from about 0.1 to about 10 hr.$^{-1}$ and a pressure of from about 1 to about 100 atmospheres absolute.

8. The process of claim 7 wherein said converting occurs in the substantial absence of an oxidizing gas.

9. The process of claim 8 wherein said converting occurs in the presence of steam.

10. The process of claim 8 wherein said oxygenated hydrocarbon is selected from the group consisting of α-methylglucoside and tetrahydrofurfuryl alcohol.

11. The process of claim 8 wherein said oxygenated hydrocarbons have an R value <1, wherein R is defined in accordance with the formula $$R = (m = 2p)/n$$

wherein m is the number of hydrogen atoms, p is the number of oxygen atoms, and n is the number of carbon atoms in said oxygenated hydrocarbon.

12. The process of claim 8 wherein said hydrocarbons are a mixture of aliphatic and aromatic hydrocarbons having a full boiling range of from about 30° to about 220° C. and are suitable for use as a motor fuel for internal combustion engines.

13. The process of claim 1 wherein said crystalline aluminosilicate zeolite is supported on a low surface area, low acidity diluent comprising silica.

14. The process of claim 13 wherein the weight ratio of crystalline aluminosilicate to diluent varies from about 0.01 to about 0.50.

* * * * *